United States Patent [19]

Neihart

[11] 4,299,574
[45] Nov. 10, 1981

[54] FABRICATION OF DENTAL RESTORATIONS

[76] Inventor: Tommy R. Neihart, 707 N. Wayne St., Apt. 101, Arlington, Va. 22201

[21] Appl. No.: 30,381

[22] Filed: Apr. 16, 1979

[51] Int. Cl.³ ............................................. A61C 11/00
[52] U.S. Cl. ..................................... 433/213; 433/37; 433/60
[58] Field of Search ....................... 433/34, 60, 42, 37, 433/38, 213

[56] References Cited

U.S. PATENT DOCUMENTS

| | | | |
|---|---|---|---|
| 2,583,170 | 1/1952 | Getz | 433/35 |
| 2,786,272 | 3/1957 | Lindley | 433/60 |
| 3,059,336 | 10/1962 | Windish | 433/58 |
| 3,495,333 | 2/1970 | Kuhn | 433/34 |
| 3,702,027 | 11/1972 | Marshall et al. | 433/33 |
| 4,161,067 | 7/1979 | Bekey et al. | 433/42 |

Primary Examiner—Robert Peshock
Attorney, Agent, or Firm—Cushman, Darby & Cushman

[57] ABSTRACT

An assembly for and a method of fabricating dental restorations. Dental impression material is disposed in a dental tray having a pair of spaced side walls, and an impression of teeth is taken. A die cavity is formed directly around the dental tray and a solidifiable plastic mass is injected into the die cavities, which mass solidifies to form dies. Vertical serrations, including alternating vertically tapered ridges and valleys, are formed on the bases of the dies during the solidification thereof, and these vertical serrations interfit with similar surfaces formed on a dental articulator to position the dies against displacement in a horizontal plane in the dental articulator, yet allowing ready removal thereof vertically when desired.

14 Claims, 8 Drawing Figures

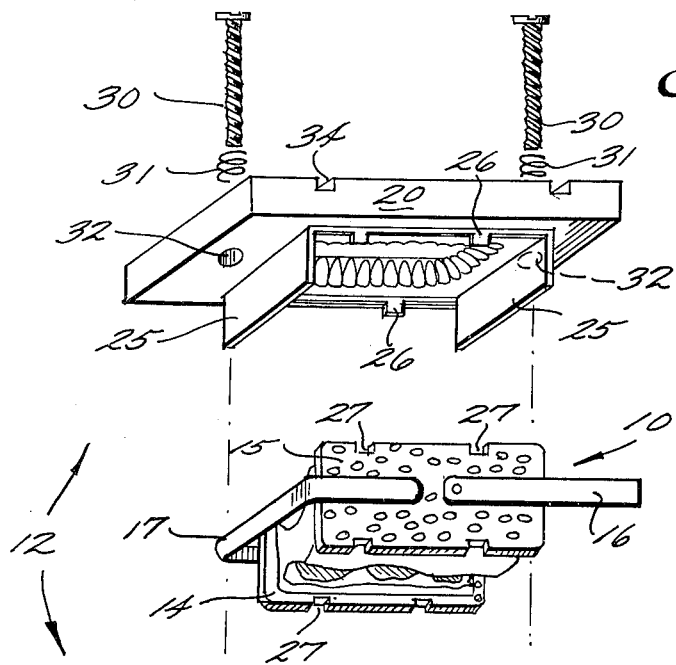
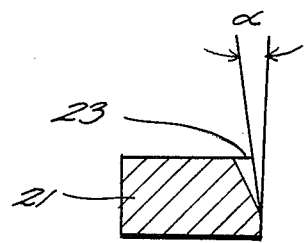
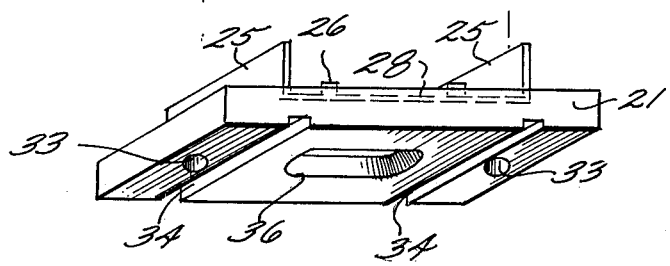
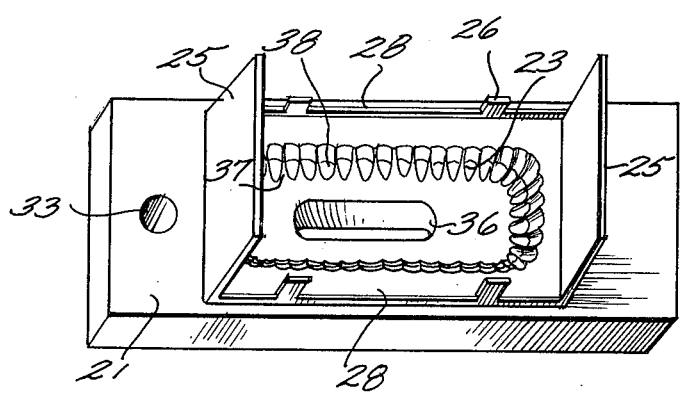
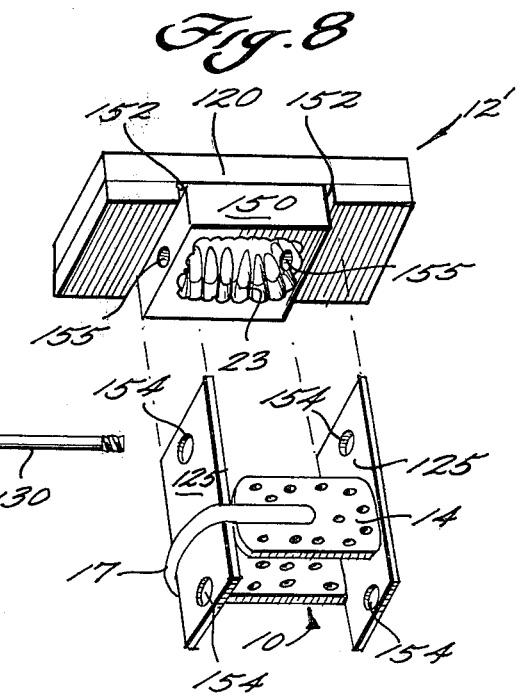

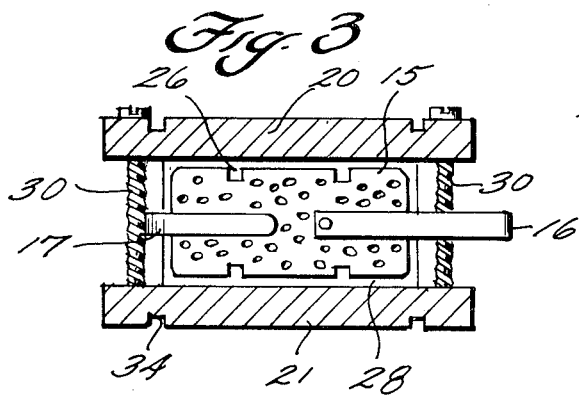
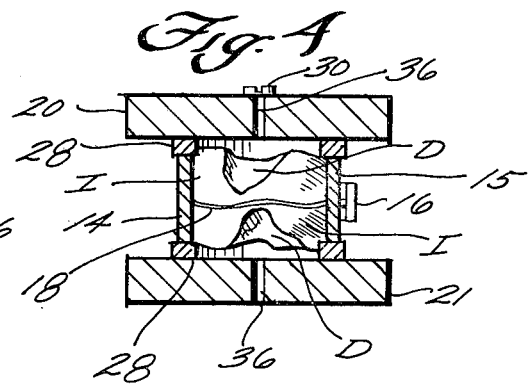
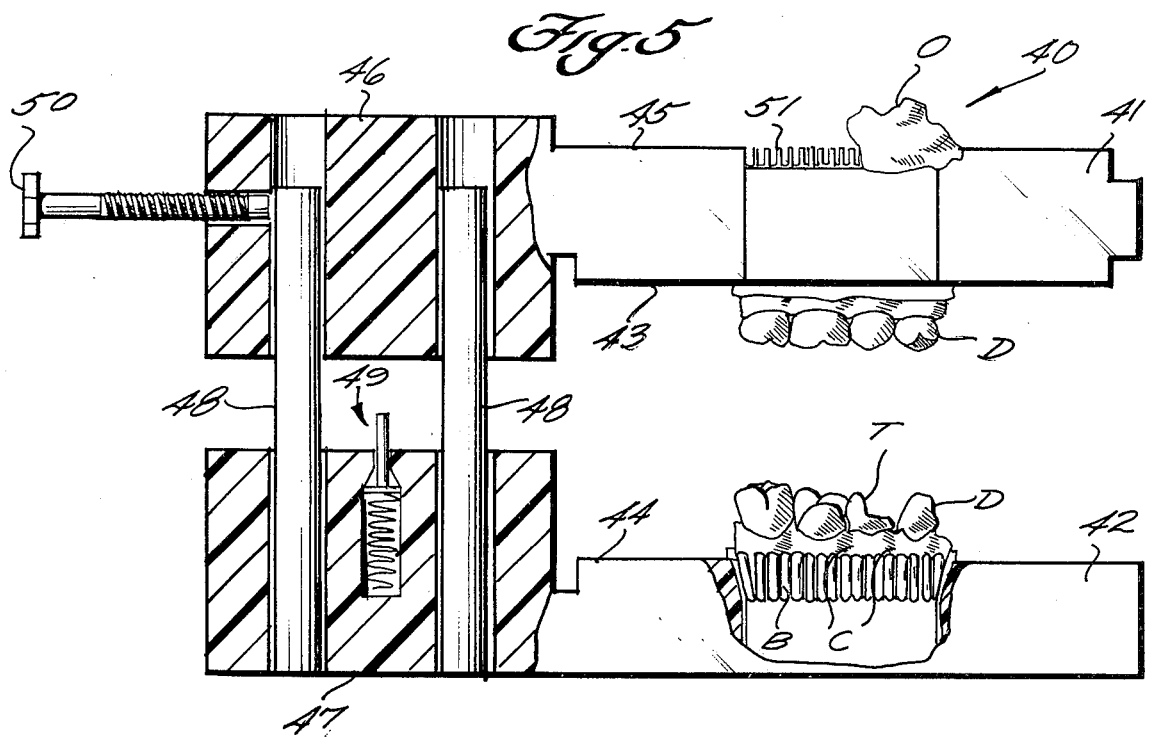
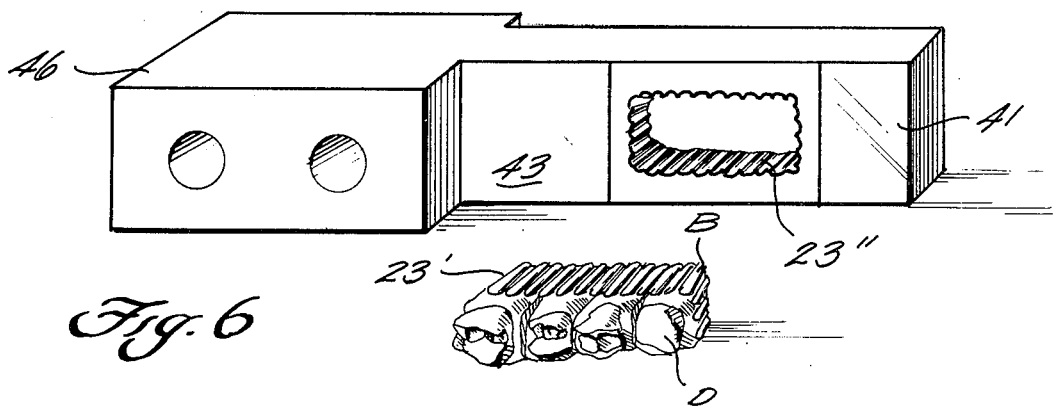

FABRICATION OF DENTAL RESTORATIONS

BACKGROUND AND SUMMARY OF THE INVENTION

The invention relates to a simplified assembly for and a simplified method of fabricating dental restorations, such as inlays, crowns, bridges, and the like. Traditionally, the fabrication of dental restorations has been a difficult and time-consuming procedure requiring a number of different operations each using different equipment, with substantial delays between some of the method steps. Oftentimes, after an impression is taken, the impression is sent to a laboratory where it is placed in a structure for forming a dental working cast, the prepared tooth is cut from the cast and a tapered pin is attached to the prepared tooth die for insertion into an opening that is formed in the working cast, and the entire working cast is then mounted on a dental articulator. According to the present invention, it is possible to eliminate some of the special equipment associated with such prior art techniques, and to greatly simplify the technique, allowing the dies to be constructed in the same work area where the dental impression is taken.

According to a method of producing dental restorations according to the present invention, a dental tray having impression material disposed therein, die cavity forming means cooperable with the dental tray to form a pair of die cavities, and a dental articulator are utilized. An impression of a person's teeth in the impression material disposed in the dental tray is formed, and the tray is removed from the person's mouth. Then the die cavity forming means are positively mounted in cooperation with the tray to form a pair of die cavities and a solidifiable plastic mass (e.g. die stone, dental cast stone, plaster of Paris, or the like) is injected into each of the die cavities, which mass solidifies to form dies. The dies are removed from the cavities once solidified and operatively mounted to the dental articulator. The dental articulator has surface manifestations (e.g. vertical serrations including alternately vertically tapered ridges and valleys) formed thereon, and surface manifestations are formed on the bases of the dies during solidification thereof to cooperate with the dental articulator surface manifestations, the surface manifestations positively positioning the dies against displacement in a horizontal plane yet allowing ready vertical removal thereof.

The dental restoration fabricating assembly according to the present invention comprises a dental tray and die cavity forming means. The dental tray includes a pair of spaced side walls, means for releasably maintaining the walls in spaced position, and a deformable divider contained by the side walls, the tray adapted to contain dental impression material (e.g. silicone impression material, hydrocolloid, or the like) therein. The die cavity forming means includes a pair of base members having continuous peripheral portions defining a cavity therein, means for mating with the dental tray side walls and base members to define operable die cavities for receipt of a solidifiable plastic mass therein, and means providing for injection of solidifiable plastic material into the die cavities formed by the dental tray, mating means, and base members. The base member continuous peripheral portions preferably comprise surface means for forming a die base having surface means that are positively positionable against displacement in a horizontal plane when disposed in a mounting structure having like surface means, yet are readily removable vertically. Such surface means preferably comprise vertical serrations including alternating vertically tapered ridges and valleys.

The assembly according to the invention preferably also comprises a dental articulator. Die holding means are formed on the dental articulator having surface means corresponding to the base member continuous peripheral portion surface means. A preferred dental articulator is of the type shown in U.S. Pat. No. 3,059,336 having a pair of parallel arms. According to the invention, one of the arms—which has die-receiving surface means formed thereon on one face—has means for mounting an occluding model on the opposite face thereof, the arm being mounted with respect to guide posts for the articulator so that the arm may be inverted and the second face linearly moved into operative association with the other arm.

It is the primary object of the present invention to provide a simplified assembly for and a simplified method of fabricating dental restorations. This and other objects of the invention will become clear from an inspection of the detailed description of the invention, and from the appended claims.

BRIEF DESCRIPTION OF THE DRAWINGS

FIG. 1 is an exploded perspective view of an exemplary dental tray and exemplary die cavity-forming means according to the present invention;

FIG. 2 is a top perspective view of a base member, and associated structure, of FIG. 1;

FIG. 3 is a side view of the structures of FIG. 1 in assembled position;

FIG. 4 is an end cross-sectional view of the structures of FIG. 1 in assembled condition;

FIG. 5 is a side view, partly in cross-section and partly in elevation, of an exemplary dental articulator for use according to the present invention, in combination with dies prepared according to the invention;

FIG. 6 is a perspective view of the top arm of the articulator of FIG. 5 with die removed;

FIG. 7 is a cross-sectional view of a part of the base of FIG. 2 illustrating the particular nature of the serrated surface means thereof; and FIG. 8 is an exploded perspective view of another embodiment of a die-cavity forming means associated with a dental tray, for practicing the invention.

DETAILED DESCRIPTION OF THE DRAWINGS

An exemplary assembly for fabricating dental restorations, according to the present invention, is illustrated in the drawings. The basic components of the assembly include a dental tray 10 and die cavity-forming means, shown generally at 12 in FIG. 1.

The dental tray 10 includes a pair of spaced side walls 14, 15 (which preferably are perforated), a retaining bar 17 or like means for releasably maintaining the walls 14, 15 in spaced position, and a deformable divider 18 (see FIG. 4) contained by the side walls 14, 15. The tray 10 is adapted to contain dental impression material I (see FIG. 4) therein, and the divider 18 can be of any material compatable with the dental impression material I, such as a piece of gauze. The dental tray 10 also includes a handle 16 for facilitating insertion and removal of the tray 10 into and from a person's mouth. The side wall members 14, 15 need not be completely straight, but may be formed as cooperating arcuate structures, and may be designed to accommodate flexible conduits from a water-cooling system, or the like, or may be otherwise modified as shown in U.S. Pat. No. 3,583,170, the disclosure of which is hereby incorporated by reference herein.

The die cavity forming means 12 includes a pair of base members 20, 21 each having continuous peripheral portions 23 defining a cavity therein. The means 12 further comprises means for mating with the dental tray side walls 14, 15, and the base members 20, 21 to define operable die cavities for receipt of a solidifiable plastic mass therein. Such mating means may comprise a pair of upstanding walls 25 formed in each base member 20, 21 on opposite sides of the cavity formed therein, and positioned to extend between the dental tray side walls 14, 15 (see FIG. 3), interlocking surface manifestations—such as pins 26 formed on ridges 28 extending from the base members 20, 21, and cooperating grooves 27 formed in the top and bottom edges of the walls 14, 15—formed on the base members 20, 21 and the dental tray side walls 14, 15, and means for maintaining the base members, dental tray, and base member upstanding walls 25 positively assembled together to form operable die cavities. Such maintaining means may take the form of a plurality of bolts 30, which may be loaded by springs 31 (see FIG. 1), which bolts pass through openings 32 in one of the base members 20 and thread into openings 33 in the other base member 21, thus operatively engaging both base members 20, 21 when in assembled condition (see FIG. 3). Additionally, grooves 34 may be provided on the exterior surfaces of the base members 20, 21 for positively locating them in an accessory mounting structure during hardening of the solidifiable plastic mass injected therein. Means are also provided—such as the openings 36—for providing injection of a solidifiable plastic material into the die cavities formed by the dental tray 10, mating means, and base members 20, 21.

The continuous peripheral portions 23 of the base members preferably comprise—as illustrated in the drawings (see FIGS. 1, 2 and 7 in particular)— surface means for forming a die base B (see FIGS. 5 and 6) having surface means that are positively positionable against displacement in a horizontal plane when disposed in a mounting structure having like surface means, yet are readily removable vertically. Such surface means preferably comprises vertical serrations including alternating ridges 37 and valleys 38 (see FIG. 2). For ease of insertion and withdrawal of the die base B into positive holding relationship with cooperating mounting means, the ridges 37 and valleys 38 are preferably tapered vertically an angle $\alpha$ (see FIG. 7), which preferably is about 2°.

The dies D are shown being formed in FIG. 4. Once the dies are formed, the bolts 30 are removed and the dies are separated from the base members 20, 21 and from the dental tray 10 and associated impression material I. The removed dies D thus have bases B with surface means 23' (see FIG. 6) formed thereon. A dental articulator 40, as illustrated in FIGS. 5 and 6, has surface means 23" formed thereon corresponding to the base members 20,21, continous peripheral portion surface means 23, which surface means 23" receive and positively locate the surface means 23' and the dies D base members B. The die D containing the prepared tooth T (see FIG. 5) is cut—as at lines C—so that the prepared tooth T is readily removable from the die D with which it is associated for ease of formation of the desired dental restoration.

A preferred dental articulator 40 for use according to the present invention is of the type shown in U.S. Pat. No. 3,059,336. This articulator 40 comprises a pair of parallel arms 41, 42, each having a first face (43, 44 respectively) with which said surface means 23" are provided. The arm 41 also has a second face 45 substantially parallel to and opposite the first face 43. The arms 41, 42 also have block portions 46, 47 associated therewith and means are provided for guiding the block portions so that they are merely linearly movable with respect to each other to provide for movement of the arm first faces 43, 44 toward operative association with each other. Such guiding means include a pair of guide pins 48 received by openings formed in the blocks 46, 47. A spring-biased pin 49 is also provided for biasing the block portions apart so that when clamping pressure is released the dies D mounted to the arms 41, 42 are moved out of engagement with each other. The arms 41, 42 may be held in any relative position desired by the locking screw 50.

The arm 41 has means 51 formed thereon for mounting an occluding model O thereon in operative relationship with the die D associated with the arm 42. When desired, the arm 41 can be removed from engagement with the guiding pins 48, and inverted so that the occluding model O will then be moved toward operative association with the die D associated with the arm 42.

Another embodiment of die cavity forming means according to the present invention is shown generally at 12' in FIG. 8. The means 12' cooperate with a dental tray 10, and include a pair of base members, only one of which—base member 120—is shown in FIG. 8, the other base member being substantially identical. A pair of side plates 125 are provided for cooperation with the ends of the walls 14, 15 of the tray 10, the plates 125 being receivable within the grooves 152 of the base members. An upstanding central portion—such as portion 150—is associated with each base member, and contains the continuous peripheral portions 23. Cooperating openings 154, 155 are formed in the plates 125 and portion 150, respectively, for receipt of bolts 130, for holding the plates 125, dental tray walls 14, 15, and base member central upstanding portions (e.g. 150) tightly together in assembled position, to form operable die cavities and to ultimately receive the solidifiable plastic mass therein.

In practicing the method according to the present invention, the tray 10—with divider 18 and dental impression material I disposed therein—is inserted into a person's mouth, and the person bites down on the impression material I leaving teeth impressions such as indicated in FIG. 4. The tray 10 is then removed from the person's mouth and the die cavity forming means 12 are operatively mounted in association therewith by moving the pins 26 into engagement with the grooves 27 and bolting the base member 20, 21 together with the bolts 30. [Or the tray 10 is mounted in operative association with the means 12']. A solidifiable plastic mass is then injected through openings 36 into one or both of the die cavities formed by the tray 10 and means 12, which mass solidifies to form dies D. The dies D, which include the vertical serrations of alternately vertically tapered ridges and valleys 23' on the base B thereof—are removed from the cavities once solidified and operatively mounted in cooperation with the surface means 23" of the dental articulator 40.

The dental impression material I is readily removed from the dental tray by removing the material from between the side walls 14, 15 apart, and the dental tray 10 and die cavity forming means 12 may then be readily reused. For working on the prepared tooth T, the die D with which it is associated is cut by severing the prepared tooth T with attached serrated base portion completely from the rest of the die D, as by cutting it along lines C (see FIG. 5).

For further fabrication of the dental restoration, an occluding model O is made by conventional techniques and is mounted on the mounting means 51 of articulator arm 41. The arm 41 is then inverted from the position illustrated in FIG. 5, and thus moves back and forth into operative association with the prepared tooth T mounted on arm 42.

It will thus be seen that according to the present invention a simplified method and assembly have been provided for the fabrication of dental restorations. While the invention has been herein shown and described in what is presently conceived to be the most practical and preferred embodiments thereof, it will be apparent to those of ordinary skill in the art that many modifications may be made thereof within the scope of the invention, which scope is to be accorded the broadest interpretation of the appended claims so as to encompass all equivalent assemblies and methods.

What is claimed is:

1. An assembly for fabricating dental restorations, comprising a dental tray including a pair of spaced side walls; means for releasably maintaining the walls in spaced position; and a deformable divider contained by the side walls, said tray adapted to contain dental impression material therein; and die cavity forming means including a pair of base members having continuous peripheral portions defining a cavity therein; means for mating with said dental tray side walls and base members to define operable die cavities for receipt of a solidifiable plastic mass therein; and means providing for injection of solidifiable plastic material into the die cavities formed by said dental tray, mating means, and base members; said mating means comprising a pair of upstanding walls formed on each base member on opposite sides of the cavity formed therein and positioned to extend between said dental tray side walls; interlocking surface manifestations formed on said base members and said dental tray side walls; and means for maintaining said base members, dental tray, and base member upstanding walls positively assembled together to form operable die cavities, said maintaining means comprising a plurality of spring-loaded bolts operatively engaging both said base members.

2. An assembly for fabricating dental restorations, comprising a dental tray including a pair of spaced side walls; means for releasably maintaining the walls in spaced position; and a deformable divider contained by the side walls, said tray adapted to contain dental impression material therein;

die cavity forming means including: a pair of base members having continuous, closed loop, peripheral portions defining a cavity therein completely contained on the side thereof by said closed loop peripheral portions, vertical serrations including alternating ridges and valleys formed along the entire extent of said peripheral portions; means for mating with said dental tray side walls and base members to define operable die cavities for receipt of a solidifiable plastic mass therein; and means providing for injection of solidifiable plastic material into the die cavities formed by said dental tray, mating means, and base members; and die holding means formed on a dental articulator having vertical serrations including alternating ridges and valleys corresponding to said base member continuous peripheral portions vertical serrations.

3. An assembly as recited in claim 2 wherein said dental tray side walls are perforated.

4. An assembly as recited in claim 2 wherein said ridges and valleys taper vertically.

5. An assembly as recited in claim 2 wherein said mating means comprise a pair of upstanding walls formed on each base member on opposite sides of the cavity formed therein and positioned to extend between said dental tray side walls; interlocking surface manifestations formed on said base members and said dental tray side walls; and means for maintaining said base members, dental tray, and base member upstanding walls positively assembled together to form operable die cavities.

6. An assembly as recited in claim 2 wherein said dental articulator comprises a pair of parallel arms each having a first face with which said surface means are provided; an enlarged block portion operatively attached to each arm; and means for guiding said block portions so that they are merely linearly movable with respect to each other to provide for movement of said arm first faces toward operative association with each other; and wherein one of said arms has a second face substantially perpendicular to said first face, said second face having means for mounting an occluding model thereon in operative alignment with the surface means formed on the other of said arms, so that said one of said arms may be inverted and said second face linearly moved into operative association with said other arm first face.

7. An assembly as recited in claim 2 wherein said means for mating with said dental tray side walls and base members to define operable die cavities comprise a pair of separable side plates detachably connectable to said base members.

8. An assembly as recited in claim 2 wherein said dental tray side walls define exterior surfaces of said die cavities, and further comprising cooperating pins and recesses formed on said base members and dental tray side walls providing interlocking thereof.

9. As assembly as recited in claim 2 wherein said means for providing for injection of solidifiable plastic material into the die cavities comprise means defining an opening in each of said base members, each of said openings extending in a dimension substantially perpendicular to said dental tray deformable divider and substantially parallel to said dental tray side walls when said dental tray is assembled with said base members.

10. An assembly for fabricating dental restorations, comprising a dental tray including a pair of spaced side walls; means for releasably maintaining the walls in spaced position; and a deformable divider contained by the side walls, said tray adapted to contain dental impression material therein; and die cavity forming means including a pair of base members having continuous peripheral portions defining a cavity therein; means for mating with said dental tray side walls and base members to define operable die cavities for receipt of a solidifiable plastic mass therein; and means providing for injection of solidifiable plastic material into the die cavities formed by said dental tray, mating means, and base members, said injection providing means comprising means defining an opening in each of said base members, each of said openings extending in a dimension substantially perpendicular to said dental tray deformable divider and substantially parallel to said dental tray side walls when said dental tray is assembled with said base members.

11. An assembly as recited in claim 10 wherein said mating means include a pair of side plates; an upstanding central portion of each of said base members; a pair of grooves formed in each of said base members for receipt of said side plates; and means for maintaining said base members, dental tray, and side plates positively assembled together to form operable die cavities.

12. A method of producing dental restorations utilizing a dental tray having impression material disposed therein, die cavity forming means cooperable with the dental tray to form a pair of die cavities, having a die mounting structure with vertical serrations including ridges and valleys and a dental articulator, said method comprising the steps of forming an impression of some, but not all, of a person's teeth in the impression material disposed in the dental tray;

removing the tray from the person's mouth and positively mounting the die cavity forming means in cooperation with the tray to form a pair of die cavities;

injecting a solidifiable plastic mass into at least one of the die cavities, which mass solidifies to form a die;

forming vertical serrations including alternative vertically tapered riges and valleys on the bases of the dies during solidification thereof;

removing the at least one die from its cavity once solidified;

cutting the prepared tooth from the formed die by severing the prepared tooth with an attached serrated base portion completely from the rest of the die; and operatively mounting the at least one die vertical serrations to the dental articulator serrated mounting structure.

13. A method as recited in claim 12 wherein the dental articulator has first and second arms that are linearly movable with respect to each other, each arm having a first face for mounting the dies thereon, and the first arm having a second face parallel to the first face, and formed to receive an occluding model thereon; said method comprising the further steps of forming an occluding model, mounting the occluding model on the articular first arm second face, and inverting the first arm so that the second face thereof is movable into operative association with the first face of the second arm.

14. A method as recited in claim 10 wherein the dental tray includes a deformable divider with dental impression material formed on each side of the divider; and wherein the injecting step is practiced by injecting the solidifiable plastic mass in a direction substantially perpendicular to the divider, with the divider disposed substantially horizontally.

* * * * *